(12) United States Patent
Fujimoto

(10) Patent No.: US 8,569,048 B2
(45) Date of Patent: Oct. 29, 2013

(54) ACTUATORS FOR CULTURING AND HARVESTING CELLS

(75) Inventor: Koji Fujimoto, Kyoto (JP)

(73) Assignee: Empire Technology Development LLC, Wilmington, DE (US)

( * ) Notice: Subject to any disclaimer, the term of this patent is extended or adjusted under 35 U.S.C. 154(b) by 397 days.

(21) Appl. No.: 12/631,623

(22) Filed: Dec. 4, 2009

(65) Prior Publication Data
US 2011/0136222 A1 Jun. 9, 2011

(51) Int. Cl.
*C12M 1/00* (2006.01)
*C12M 3/00* (2006.01)

(52) U.S. Cl.
USPC .................. 435/289.1; 422/552; 422/553

(58) Field of Classification Search
USPC ........ 435/289.1, 325; 29/527.1; 422/552, 553
See application file for complete search history.

(56) References Cited

U.S. PATENT DOCUMENTS

| 5,705,813 | A | 1/1998 | Apffel et al. | |
|---|---|---|---|---|
| 6,048,734 | A | 4/2000 | Burns et al. | |
| 6,299,907 | B1 | 10/2001 | Seib et al. | |
| 6,428,811 | B1 | 8/2002 | West et al. | |
| 2003/0156953 | A1* | 8/2003 | Chinn et al. | 417/322 |
| 2003/0156991 | A1 | 8/2003 | Halas et al. | |
| 2007/0196281 | A1 | 8/2007 | Jin et al. | |
| 2008/0142501 | A1 | 6/2008 | Morioka et al. | |
| 2008/0227664 | A1* | 9/2008 | Honma et al. | 506/39 |
| 2008/0241262 | A1 | 10/2008 | Lee et al. | |
| 2009/0258073 | A1 | 10/2009 | Tishin et al. | |
| 2011/0036431 | A1 | 2/2011 | Lee | |
| 2011/0136222 | A1 | 6/2011 | Fujimoto | |

FOREIGN PATENT DOCUMENTS

| JP | 200729249 | 9/2007 |
|---|---|---|
| WO | WO 2005092286 | 10/2005 |

OTHER PUBLICATIONS

Noritake Col, Limited "Ceramic Heater: Far-infrared Ceramic Heater" Online: http://www.noritake.co.jp/eng/eeg/heat/product/ensekigaisen/pdf/ceramicheat.pdf.
Yoshihito Osada, et al "Spontaneous Motion of Amphoteric Polymer Gels on Water" Jpn. J. Appl. Phys. vol. 34 (1995) pp. L511-L512, Part 2, No. 4B, Apr. 15, 1995.
Xiuli Zhao, et al "A kind of smart gold nanoparticle-hydrogel composite with tunable thermo-switchable electrical properties" New Journal of Chemistry, 2006, 30, pp. 915-920.
Xiuli Zhao, et al "Thermoswitchable Electronic Properties of a Gold Nanoparticle/Hydrogel Composite" Macromolecular Rapid Communications, 2005, 26, pp. 1784-1784.
Mathias Brust, et al "Synthesis of Thiol-derivatised Gold Nanoparticles in a Two-phase Liquid-Liquid System" J. Chem. Soc., Chem. Commun., 1994 pp. 801-802.
Jun-Hyun Kim, et al "Thermo-Responsive Hydrogel-Coated Gold Nanoshells" Intl. Conf. on Biomedical and Pharmaceutical Engineering 2006 (ICBPE 2006), Dec. 11-14, 2006 pp. 271-275.
Jun-Hyun Kim, et al "Thermo-Responsive Hydrogel-Coated Gold Nanoshells for in Vivo Drug Delivery" Journal of Biomedical & Pharmaceutical Engineering 2:1 (2008) pp. 29-35.

(Continued)

*Primary Examiner* — Michael Hobbs
(74) *Attorney, Agent, or Firm* — Workman Nydegger

(57) ABSTRACT

Actuator units, arrangements of actuator units and methods for manufacturing and using actuator units are provided. The actuator includes a core having a shell at least partially surrounding the core. The core is able to be stimulated to expand through at least one opening of the shell to provide a lifting action. This lifting action can be applied to harvest target cells.

13 Claims, 6 Drawing Sheets

(56) References Cited

OTHER PUBLICATIONS

Kazutoshi Haraguchi, et al "Effects of Clay Content on the Properties of Nanocomposite Hydrogels Composed of Poly(N-isopropylarcrylamide) and Clay" Marcomolecules 2002, 35, 10162-10171.

Y. Nagata, et al "Soft Actuators", NTS (2004).

Y. Furuya, et al "Next-Generation Actuator Materials and Devices" CMC Press (2006) Chapter 7.

Y. Nakano "Functions of Polymer Gels" CMC Press (1999) 62-64.

Hiroyuki Sasase, et al "Regulation of temperature-response swelling behavior of interpenetrating polymer networks composed of hydrogen bonding polymers" Makromol. Chem., Rapid Commun. 13, (1992) 577-581.

Ryo Yoshida, et al "Drug Release Profiles in the Shrinking Process of Thermoresponsive Poly(N-isopropylacrylamide-co-alkyl methacrylate) Gels" Ing. Eng. Chem. Res. 1992, 31, 2339-2345.

Yoshiharu Hirose "The Response of Ionic Gels Upon Electric Fields" Online [http://www.tytlabs.co.jp/japanese/review/rev272pdf/272_001_hirose.pdf] vol. 27, No. 2 (Jun. 1992).

Rama Venkatasubramanian, et al "Thin-film thermoelectric devices with high room-temperature figures of merit" Nature, vol. 413, Oct. 11, 2001 pp. 597-602.

Karl Kratz, et al "Structural changes in PNIPAM microgel particles as seen by SANS, DLS and EM techniques" Polymer, 42, (2001), 6631-6639.

Robert Pelton "Temperature-sensitive aqueous microgels" Advances in Colloid and Interface Science, 85, (2000) 1-33.

Australian Patent Office; International Search Report and Written Opinion from International application No. PCT/KR2010/005216; mailed Oct. 28, 2010.

Jun-Hyun Kim, et al "Discrete Thermally Responsive Hydrogel-coated Gold Nanoparticles for Use as Drug-delivery Vehicles"Drug Development Research, Special Issue: Nanobiotechnology, vol. 67, Issue 1, pp. 61-69, Jan. 2006.

Reynolds A. Frimpong, et al "Synthesis and Temperature Response Analysis of Magnetic-Hydrogel Nanocomposites" Journal of Biomedical Materials Research Part A, vol. 80A, Issue 1, pp. 1-6, Jan. 2007.

Noritake Col, Limited "Ceramic Heater: Far-infrared Ceramic Heater" Online: http://www.noritake.co.jp/eng/eeg/heat/product/ensekigaisen/pdf/ceramicheat.pdf; available at least as of Aug. 2, 2009.

U.S. Appl. No. 12/540,875, Feb. 9, 2012, Arundale, Robert K. Office Action: Inventor: Kwangyeol Lee, pp. 6.

Lavine K. B. et al., "Swellable molecularly imprinted polyN-(N propyl)acrylamide particles for detection of emerging organic contaminants using surface plasmon resonance spectroscopy," TALANTA, vol. 72, Issue 3, pp. 1042-1048, (2007).

U.S. Appl. No. 12/540,875, Dec. 14, 2012, Office Action, Inventor: Kwangyeol Lee.

Merriam-Webster; http://www.merriam-webster.com/dictionary/dispersed, Accessed Aug. 21, 2012.

U.S. Appl. No. 12/540,875, May 1, 2012, Office Action, Inventor: Kwangyeol Lee.

U.S. Appl. No. 12/540,875, Sep. 13, 2012, Office Action, Inventor: Kwangyeol Lee.

U.S. Appl. No. 12/540,875, mailed Mar. 22, 2013, Notice of Allowance.

\* cited by examiner

ACTUATORS FOR CULTURING AND HARVESTING CELLS

TECHNICAL FIELD

Embodiments described herein relate to culturing and harvesting cells. More particularly, nano-sized actuators are used to culture and harvest cells.

BACKGROUND

Adherent cell culture systems require a surface on which to culture cells, such as a culture container or microcarrier (such as gelatin, porous glass, collagen or cellulose). The surface may also be coated with an extracellular matrix to increase adhesion properties. Feeder cells may also be used to coat the surface to provide a more adherent surface as well as nutrients to culturing cells. When the cultured cells are ready to harvest, usually an enzyme is used to separate the cultured cells from the surface. However, use of enzymes or other chemicals to separate cultured cells from the surface can cause damage to the cultured cells.

DETAILED DESCRIPTION

Figure 1A:
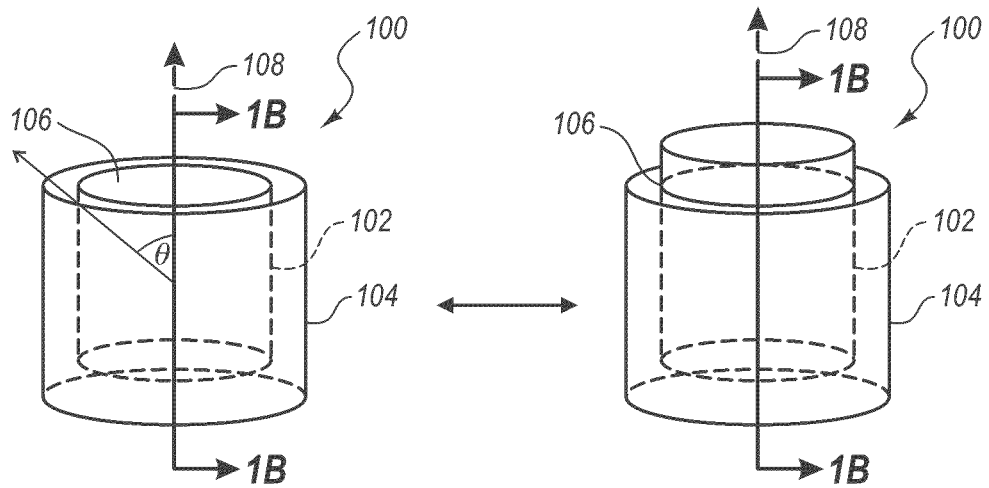
FIG. 1A is a schematic of an illustrative embodiment of an actuator.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The following disclosure generally relates to actuator units or actuators, arrangements of actuators, and methods for manufacturing and using actuators. One aspect includes actuators that generally include a core at least partially surrounded by a shell. The shell has at least one opening to expose at least a first portion of the core. The core is made of a stimuli-responsive polymer that responds to an applied stimulus (or stimuli) to become activated or deactivated. When the core is placed in the activated state, at least a first portion of the core expands and extrudes out of the shell and passes through an opening of the shell. In the activated state, at least the first portion of the core is located outside a perimeter of the shell. The core can also be deactivated to contract the first portion to be placed within a perimeter of the shell again.

The stimuli-responsive polymer of the core and/or shell can be selected to react to one or more stimuli. The stimuli-responsive polymer can thus include one or more of a thermo-responsive polymer, or a photo-responsive polymer, or a combination thereof. Examples of thermo-responsive polymers include, but are not limited to, poly-N-isopropylacrylamide (PNIPAAm), poly-vinylmethylether (PVME), poly-dimethyl acrylamide (PDAAm), poly-methacrylate (PMA), poly-acrylic acid (PAA), or a combination thereof. In one embodiment, the polymer of the core and/or shell includes Au or Fe particles, or alloyed versions thereof, dispersed in the polymer. The Au or Fe particles can be stimulated by heat or light, providing both thermo-responsive and photo-responsive actuators. Further details regarding illustrative materials, sizes, and/or shapes of the actuators are disclosed further below with reference to the drawings.

The following provides a brief summary of the operation of the actuators, which is described in further detail below. One or more actuators are placed on a surface. The actuators can be bonded to the surface. The actuators can also be bonded to each other. The actuators can operate independently of each other. One or more target cells can be located on the actuators to be cultured. As used herein, the term "target cell" generally refers to a cultured cell that has matured and is ready for harvesting. However, "target cell" more broadly refers to any cell that is desired to be harvested for any reason. In one embodiment, the target cell may be a cultured cell that has not grown well in the culture, or may have died, where it is desired to remove that cell from the culture. In another embodiment, the target cell may be a feeder cell that contributed to culturing of other cells, but is ready to be removed from the culture. These and any other type of cell may also be located on actuators. Thus, "harvesting" in this context is used broadly to refer to any removal of any cell from a culture. It will be appreciated that the actuators greatly assist in the harvesting of target cells, whether they be cultured cells, dead cells, feeder cells or any other cell desired to be removed from the culture.

Thus, another aspect includes a method for harvesting target cells. The method includes applying one or more stimuli to one or more actuators, each actuator having a core and a shell at least partially surrounding the core, where the shell has at least one opening. The method causes at least a first portion of the core to expand through the opening of the shell such that the first portion of the core is located outside a perimeter of the shell. The method may also cause at least the first portion of the core to contract such that the first portion of the core is substantially contained within a perimeter of the shell.

Some embodiments are directed to actuators that are used in systems for culturing and harvesting target cells. FIG. 1A is a schematic of an illustrative embodiment of an actuator 100. Actuator 100 has a core 102 and a shell 104 at least partially surrounding the core. The shell 104 has at least one opening 106 positioned so that the core 102 is exposed through the opening 106. In one embodiment, the opening 106 is positioned substantially orthogonal to a longitudinal axis 108 of the actuator 100. However, the opening 106 can be formed at any location of the shell 104. For example, the opening 106 can be positioned substantially orthogonal to an axis formed at an angle θ to the longitudinal axis 108. The angle θ can be from about 0° to about 90°, or about 10° to about 80°, or about 20° to about 70°, as illustrative examples. While only one opening 106 is shown, shell 104 may include more than one opening 106. For example, the shell 104 may include an opening 106 both at the top of the shell 104 and the bottom of the shell 104.

The size of the opening 106 depends on the specific use of the actuator 100. For examples for actuators 100 being used with larger target cells, the opening 106 may be larger than for actuators 100 being used for smaller target cells. The shape of the opening 106 can be any polygonal shape including, but not limited to, circular, elliptical, square, triangular, or the like. Illustrative sizes for the opening 106 are described below. In one embodiment, the shell 104 substantially covers the core 102 except for the opening 106. Illustratively, the shell 104 may cover about 80 percent to about 95 percent of the core 102, or about 70 percent to about 95 percent of the core 102, or about 60 percent to about 95 percent of the core 102, as illustrative examples. Other configurations are also possible as will be understood by those with skill in the art.

Figure 1B:
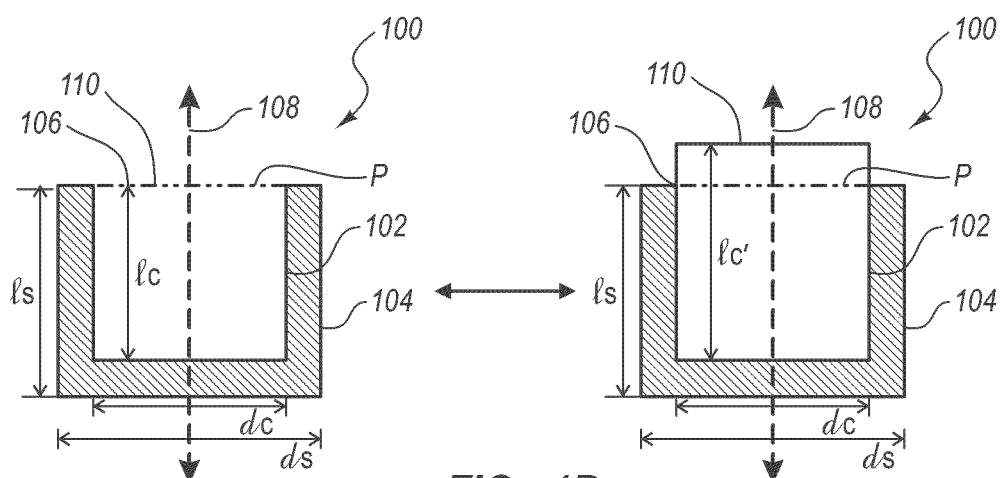
FIGS. 1B and 1C are a cross-sectional views of the actuator shown in FIG. 1A, showing a chemical principle of operation.

At least the core 102 comprises a stimuli-responsive polymer having a shape and/or size configured to expand or contract in response to one or more stimuli. FIG. 1B is a cross-sectional view of the actuator shown in FIG. 1A. FIGS. 1A and 1B together show a chemical principle of operation illustrating how an actuator 100 can be activated and/or deactivated. On the left, the actuator 100 is in a deactivated or resting state in which the core 102 has a resting length ($l_c$ in FIG. 1B). In a deactivated state, at least a portion 110 of the core 102 is contracted such that the portion 110 of the core 102 is substantially contained within a perimeter P of the shell 104. In embodiments where the shell 104 has a single opening 106, when the portion 110 of the core 102 is contained in the shell 104, generally, the only way for the core 102 to change shape is to go through opening 106.

In an activated state (on the right), the stimuli cause at least the portion 110 of the stimuli-responsive polymer of the core 102 to expand through the opening 106 of the shell 104 such that at least the portion 110 of the core 102 is located outside the perimeter P of the shell 104, causing the core 102 to have an expanded length $l_c'$. The stimuli-responsive polymer of the core 102 is reversibly responsive so that after the core 102 is placed in an activated state, the stimuli (or lack thereof) cause the stimuli-responsive polymer of the core 102 to contract such that the portion 110 of the core 102 is substantially contained within perimeter P of the shell 104.

In one embodiment, the shell 104 is rigid to hold the core 102 stably as the core 102 expands and contracts between an active and a deactivated state. FIGS. 1A and 1B show an illustrative embodiment where the shell 104 does not change in size as the actuator 100 goes from a deactivated to an activated state. In this embodiment, when the actuator 100 is placed in the activated state, the shell 104 does not change such that the core 102 expands through the opening 106 along the longitudinal axis 108 only. However, material of the shell 104 may be such that the interior of the shell 104 is slightly conformable such that when the actuator 100 is placed in an activated state, the core 102 expands both along the longitudinal axis 108 through the opening 106 and also transverse to the longitudinal axis of the actuator 100.

Figure 1C:
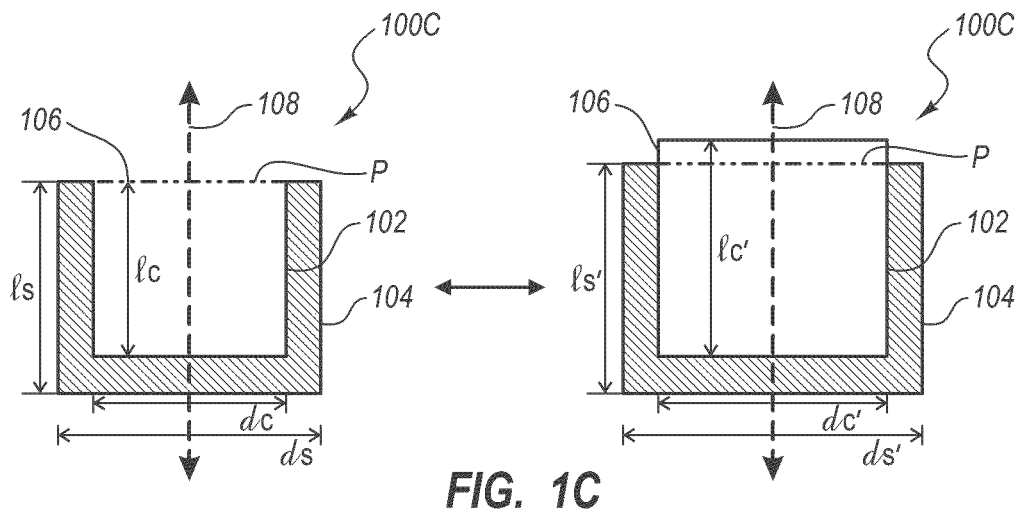

In one embodiment, the shell 104 may also have a stimuli-responsive polymer having a shape and/or size configured to expand or contract in response to one or more stimuli. From a deactivated state, the stimuli cause the stimuli-responsive polymer of the shell 104 to expand into an activated state. Similarly, from an activated state, the stimuli cause the stimuli-responsive polymer of the shell 104 to contract back to the deactivated state. The stimuli to activate the core and the stimuli to activate the shell may be the same or different stimuli, as described further below. FIG. 1C is an illustrative embodiment of an actuator 100C in which both the core 102 and shell 104 expand during the activation phase. FIG. 1C illustrates that a diameter $d_c$ and length $l_c$ of the core 102 can increase to $d_c'$ and $l_c'$ during activation of the actuator 100C. Further, a diameter $d_s$ and length $l_s$ of the shell 104 can increase to $d_s'$ and $l_s'$ during activation of the actuator 100C. In other words, upon being placed in an activated state, both the core and the shell expand both along the longitudinal axis 108 and also transverse to the longitudinal axis 108.

Other variations are possible in light of the disclosure herein. For example, depending on the number of openings 106 in the shell 104, or depending on the shape of the actuator 100, a size and/or shape of either the core and/or the shell can expand along any angle θ with respect to the longitudinal axis 108 and/or transverse to the longitudinal axis 108.

Embodiments where the shell 104 has expanding/contracting capabilities may also come into play during manufacture of the actuator 100, as described below. That is, the expanding/contracting capabilities may be used during manufacture of the actuator 100, while the shell may remain substantially rigid during the actual operational use of the actuator 100.

FIGS. 1A and 1B thus show an actuation operation of actuator 100. The actuation operation is generally used during culture of target cells. In one embodiment, a plurality of actuators 100 are arranged on a surface and target cells are placed on top of the actuators 100 to mature and become cultured. Initially, the actuators 100 are placed in a deactivated position in which at least the portion 110 of the core 102 that is exposed through the opening 106 of the shell 104 is contained within a perimeter P of the shell 104. When one or more target cells are ready for harvesting, one or more actuators 100 are activated so that at least the first portion 110 of the core 102 expands to be extruded through the opening 106 of the shell 104 and outside the perimeter P of the shell 104. The lifting action caused by the portion 110 of the core 102 as it extrudes through the opening 106 is sufficient to help break the adhesion between the target cell located on the actuator 100 and the top of the actuator 100. In one embodiment, a top surface of one or more actuators 100 may be coated with an adhesive promoting material, including, but not limited to, extracellular matrix, a growth medium (including nutrients), or the like. The lifting action can also break adhesion between target cells and other cells adjacent to the target cell. The lifting action can be repeated like a piston action. This process is described further below.

The actuators 100 can be used in one embodiment to define culturing boundaries. In one embodiment, for example, one or more actuators 100 can be positioned in a patterned design and a first cell type is then cultured over the patterned design optionally to confluency. The one or more actuators 100 positioned in the patterned design can then be placed in an activated state so that a portion 110 of the core 102 of each actuator 100 is extruded through the opening 106, detaching cells from the patterned actuators 100. When in the activated state, the patterned design serves to designate a boundary of a cell culture because cells are unable to adhere to the actuators 100 that are in the activated state, thus creating a natural boundary for cell culturing. Another cell type can then be seeded over the same surface. Typically, these subsequently seeded cells will adhere only to the exposed actuators 100, allowing the second seeded cells to grow in a well-ordered pattern.

In another example, a number of actuators 100 can be positioned in linear, semi-linear, curvilinear fashion for patterned cell culture. In one embodiment, a number of actuator units (see, e.g., 400 in FIG. 4) can be placed on the bottom of a culture container. The actuator units 400 arranged in the culture dish can then be shaped for facilitating patterned cell culture. To make the shape, actuator units 400 of cylindrical shape and part of each actuator unit 400 may be cut by laser with a set angle θ to form an actuator 100 having an opening 106. As mentioned above, the angle θ can be essentially any angle from about 0° to about 90°, or about 10° to about 80°, or about 20° to about 70°. Cells can then be seeded over the angled actuators 100, allowing the cells to grow in a well-ordered pattern.

Figure 2A:
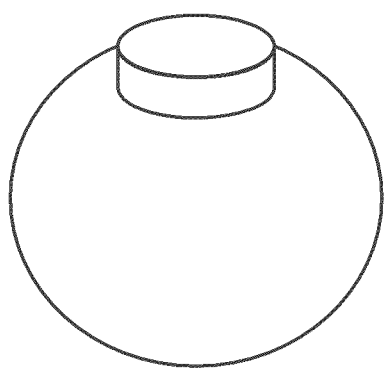
FIGS. 2A through 2C are schematics of illustrative embodiments of actuators.
Figure 2B:
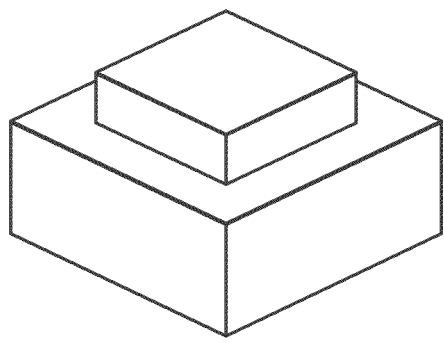
Figure 2C:
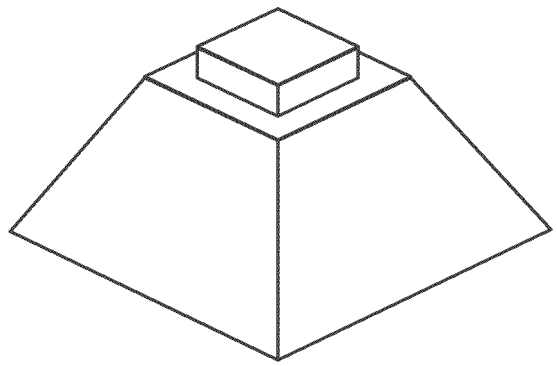

While FIGS. 1A and 1B show the shape of the core 102 and the shell 104 of the actuator 100 as being cylindrical, the shape of the actuators may be configured to be any of a variety of shapes, depending on the particular application or use of the actuators. FIG. 2A through 2C are schematics of illustrative embodiments of actuators having various shapes other than cylindrical. The actuator 120A of FIG. 2A is spherical in shape, while the actuator 120B in FIG. 2B is cubical in shape, and the actuator 120C in FIG. 2C is pyramidal in shape. In each of these illustrative embodiments, a core and a shell can operate substantially similarly to that as described above and below. However, for purposes of describing the rest of the disclosure, the cylindrical shape of FIG. 1A will be used.

Referring back to FIGS. 1B and 1C, illustrative dimensions of the cylindrical-shaped actuator 100 will be described. It will be appreciated that these illustrative dimensions are provided by way of example only and that illustrative dimensions can generally apply to other shaped actuators or be varied as appropriate, as appreciated by those of skill in the art. A resting length $l_c$ of the core 102 may be about 300 nm to about 4.5 mm. During the activated state, an active length $l_c'$ of the core 102 may be about 350 nm to about 9 mm. During the deactivated state, a resting diameter $d_c$ of the core 102 can be about 450 nm to about 4.8 mm. In embodiments where the core 102 is able to expand transverse to the longitudinal axis 108 of the actuator 100, in the activated state, the diameter $d_c'$ of the core 102 is about 480 nm to about 5.1 mm.

Illustrative dimensions of the shell 104 are as follows: During the deactivated state, a resting diameter $d_s$ of the shell 104 of the actuator 100 can be about 500 nm to about 5 mm. In embodiments where the shell 104 is able to contract/expand, the diameter $d_s'$ in an activated state can be about 530 nm to about 5.3 mm. A resting length $l_s$ of the shell 104 can be about 450 nm to about 4.8 mm. In embodiments where the shell 104 is able to contract/expand, an actuated length $l_s'$ of the shell 104 can be about 460 nm to about 4.9 mm.

Generally, a larger shell/core requires a longer amount of time to phase between the deactivated and activated states. Similarly, a smaller shell/core will phase more quickly between the deactivated and activated states. The size of the actuator can thus provide added flexibility to systems using the disclosed actuators to enable a bioengineer to select the speed of phase change based on the actuator size. A diameter of a core and/or shell can thus be selected based on a desired speed of response of the stimuli-responsive polymer of the core and/or shell, where typically a larger diameter core/shell responds slower than a smaller diameter core/shell.

The stimuli-responsive polymer of the core 102 and/or shell 104 can be selected to react to one or more stimuli. The stimuli-responsive polymer can thus include one or more of a thermo-responsive polymer, or a photo-responsive polymer, or a combination thereof.

When the stimuli-responsive polymer of the core 102 and/or shell 104 is a thermo-responsive polymer, the thermo-responsive polymer can be one or more of poly-N-isopropylacrylamide (PNIPAAm), poly-vinylmethylether (PVME), poly-dimethyl acrylamide (PDAAm), poly-methacrylate (PMA), poly-acrylic acid (PAA), or a combination thereof. Thermo-responsive polymers change phase at low critical solution temperature (LCST). A slight change of temperature can change the property of the thermo-responsive polymer so that the actuator 100 can be activated. The temperature at which the polymer changes phase can be controlled by using co-polymers by adding other polymers, such as acrylamide, to a thermo-responsive polymer.

In one embodiment, heat may be used to induce a phase change of the actuator 100. When poly-dimethyl acrylamide and poly-acrylic acid are used to prepare a copolymer for a shell 104 or core 102 of an actuator 100, this copolymer contracts below the LCST temperature and expands above the LCST temperature. Thus, heat can be used to induce the core 102 to expand to the activated state. In one embodiment, heat at a temperature of about 38° C. to about 41° C. is applied to heat the actuator 100. The heating temperature just needs to be higher than the LCST temperature of the thermo-responsive polymer.

Similarly, cooling may be used to induce a phase change of the actuator 100. When NIPAAm and poly-methacrylate are used as a copolymer for the actuator, this copolymer contracts above LCST temperature and expands below LCST temperature. Thus, cooling can be used to induce the core to expand to the activated state. In one embodiment, temperature of about 30° C. to about 34° C. is used to cool the actuators. The cooling temperature just needs to be less than the LCST temperature of the thermo-responsive polymer.

In one embodiment, the polymer of the core 102 and/or shell 104 includes Au or Fe particles, or alloyed versions thereof, dispersed in the polymer. In one embodiment, the polymer including Au or Fe particles can be one or more of poly-N-isopropylacrylamide (PNIPAAm), poly-vinylmethylether (PVME), poly-dimethyl acrylamide (PDAAm), poly-methacrylate (PMA), poly-acrylic acid (PAA), or a combination thereof. In a specific embodiment, the polymer that includes the Au or Fe particles is PNIPAAm. In one embodiment, the shell 104 includes Au or Fe particles, while the core 102 does not include Au or Fe particles. Where the shell 104 includes Au or Fe particles, the Au or Fe particles can be heated. Since the shell 104 surrounds the core 102, upon stimulating the Au or Fe particles in the shell 104, the shell 104 is able to heat the core 102 as well. In another embodiment, both the shell 104 and the core 102 include Au or Fe particles such that both the shell 104 and core 102 are heated by the Au or Fe particles. In one embodiment, the shell 104 and core 102 are made from the same polymer having Au or Fe particles located therein.

The chemical principle of operation is also similar to that of FIGS. 1A and 1B when the shell 104 and/or core 102 contain Au or Fe particles. Polymers containing Au or Fe particles can be both thermo-responsive and photo-responsive. When heat or light is radiated on the actuator 100, the Au or Fe particles heat up to a higher temperature, causing the surrounding polymer to also heat up. Thus depending if the polymer expands at higher temperature, the Au or Fe particles can be heated or irradiated with light to heat the polymer. If the polymer contracts at higher temperature, the Au or Fe particles can be heated or irradiated to heat the polymer to form an opposite chemical response. This enables both a thermo-responsive and a photo-responsive way to activate/deactivate the actuators 100. Since the same polymers recited above can be combined with Au or Fe particles, the same illustrative temperature ranges also apply.

In some embodiments, the Au or Fe particles can be heated by applying near infrared (NIR) radiation having a wavelength of, for example, about 700 nm to about 1,400 nm, or about 725 nm to about 1,000 nm, or about 750 nm to about 800 nm, as illustrative examples. Particularly, when Au or Fe particles are dispersed in a polymer, the polymer may be more reactive to light than without the Au or Fe particles, making a photo-responsive stimulus a beneficial option if a quick reaction time is needed. The polymer in which the Au or Fe particles are dispersed will expand or contract depending on the LCST temperature. The process of hydration and dehydration is completely reversible, allowing the actuator 100 to be activated/deactivated by switching the NIR radiation on/off. An irradiation device providing NIR radiation can operate slightly above physiological temperature, making a localized heating safe for cellular applications. The NIR radiation can also pass safely through tissue and water without adversely affecting the areas through which the NIR radiation passes. Any suitable NIR irradiator unit can be used, such as those that are readily commercially available.

In embodiments that include an LCST temperature that requires heating, the NIR radiation can be activated when heating is required to expand the polymer. In embodiments that include an LCST temperature that requires cooling, the NIR radiation can be activated and maintained active during culture to keep the actuators 100 at a higher temperature. Then, when the core 102 is desired to be expanded, the NIR radiation can be turned off, cooling the actuators 100 and causing the core 102 to expand. Thus, the amount of time that the NIR radiation is applied depends on the type of polymer. In one embodiment, the NIR radiation can be applied for 1 second to about 30 seconds. In another embodiment, the NIR radiation can be applied for a period of days to heat the actuators so that the core 102 does not expand while the cells are culturing.

Another example of a photo-responsive polymer that can be used with or without Au or Fe particles includes co-polymer particles formed from N-isopropylacrylamide and acrylic acid (NIPAAm-co-AA) that responds to UV light. As described below, NIPAAm-co-AA can be useful in manufacturing the actuators disclosed herein.

Illustrative methods for operating the actuators 100 are also shown in FIGS. 1A and 1B. The method includes applying one or more stimuli to one or more actuators 100. As discussed above, each actuator 100 has a core 102 and a shell 104 at least partially surrounding the core 102, the shell 104 having at least one opening 106. Because the core 102 is a stimuli-responsive polymer, the core 102 is configured to expand or contract in response to the one or more stimuli. The method includes causing the stimuli-responsive polymer of the core 102 to expand through the opening 106 of the shell 104 such that at least a portion 110 of the core 102 is located outside a perimeter P of the shell 104 to be accessible to lift one or more target cells. Illustrative methods further include removing one or more target cells from the portion 110 of the core 102 that lifts the one or more target cells. Further, methods include causing the stimuli-responsive polymer of the core 102 to contract such that the portion 110 of the core 102 is substantially contained within a perimeter P of the shell 104 after the one or more target cells have been removed.

Figure 3:
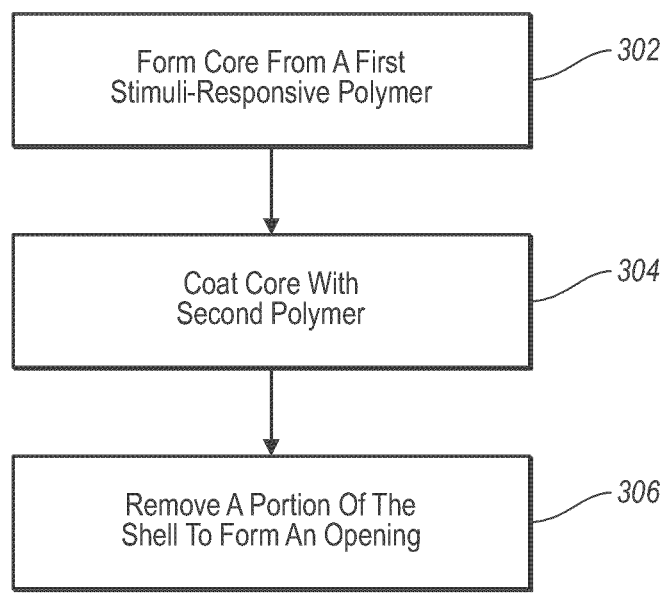
FIG. 3 is an illustrative method for manufacturing actuators.

Various methods can be used to form the actuators. FIG. 3 illustrates an illustrative method for forming an actuator using different polymers for the core and the shell. Numerals from FIGS. 1A and 1B will be used to illustrate the method. At 302, a core 102 is formed from a first stimuli-responsive polymer, for example, using free radical polymerization or a mold. At 304, the core 102 is coated with a second polymer to form a shell 104, for example, by immersing the core 102 in the second polymer.

In embodiments having Au or Fe particles dispersed in the shell 104 and/or core 102, the Au or Fe particles can be mixed in the polymer before forming the shell 104 and/or core 102. In one embodiment, the Au or Fe particles can be functionalized with a vinyl group to allow the Au or Fe particles to bond covalently to the polymer.

At 306, a portion of the shell 104 is removed to form at least one opening 106. In one embodiment, the opening 106 is arranged substantially orthogonal to a longitudinal axis 108 of the shell 104. The opening 106 of the shell 104 also exposes the first stimuli-responsive polymer of the core 102. Various methods may be used to remove the portion of the shell 104 including, but not limited to, a laser cutter, a water jet cutter, machining in a liquid $N_2$ atmosphere, or a combination thereof. Any of these methods can be used to remove portions of shells 104 for a large number of actuators 100 simultaneously.

In one embodiment, the second polymer that forms the shell 104 is a stimuli-responsive polymer so that after the second polymer is applied, a stimulus can be applied to the coating to harden the coating. The stimulus can include, but is not limited to, a heating/cooling device, or a photo-generating device, or the like. In one embodiment, the second polymer responds to UV radiation, heating, or cooling, or the like, that causes the second polymer of the shell 104 to harden. In embodiments where the shell 104 is hardened, hardening can occur before or after removing the portion of the shell 104 that forms the opening 106.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

Figure 4:
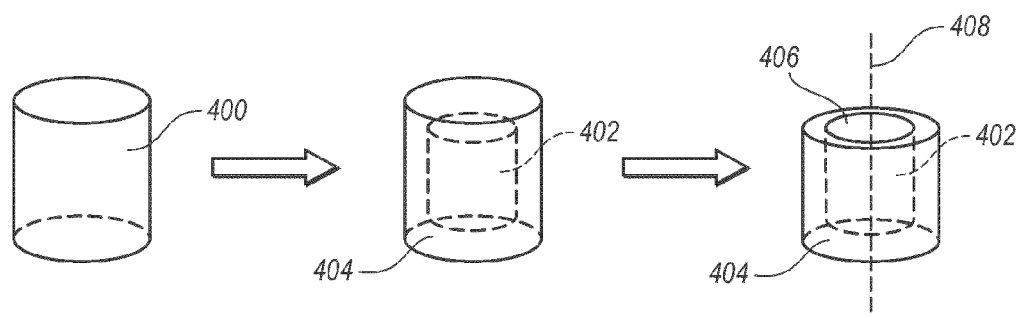
FIG. 4 is another illustrative method for manufacturing actuators.

FIG. 4 is another illustrative embodiment for a method for manufacturing actuators for use in harvesting target cells where the same stimuli-responsive polymer is used to form both the core and the shell (i.e., a monomer). FIG. 4 shows that a first stimuli-responsive polymer is used to form an actuator unit 400. A first stimulus is applied to the actuator unit 400 to harden an outer layer 404 of the first stimuli-responsive polymer, forming an unreacted inner portion 402. The stimulus can be any of the stimuli described above or a combination of stimuli.

The hardened outer layer 404 of the first stimuli-responsive polymer thus forms a shell and the unreacted inner portion 402 forms a core. A portion of the shell 404 is then removed to form at least one opening 406. In one embodiment, the opening 406 can be formed substantially orthogonal to a longitudinal axis 408 of the shell 404 to newly expose the expandable core 402. The portion of the shell 404 can be removed using any of the methods described above. When the shell 404 is hardened properly, during operation of the actuator, when a stimulus is applied to the core 402, the shell 404 does not change a shape and/or size while the core 402 is able to change a shape and/or size at least in the longitudinal direction and in some cases, the shell 404 prevents the core 402 from expanding in a transverse direction.

Materials and processes for manufacturing actuators according to the illustrative method of FIG. 4 is provided herein. N-Isopropylacrylamide (NIPAAm) was obtained from Fisher Scientific Inc. (Fair Lawn, N.J., USA) and re-crystallized from hexane. N,N'-Methylenebis(acrylamide) (MBA), acrylic acid (AA), potassium persulfate (KPS), sodium dodecyl sulfate (SDS) and poly(methyl methacrylate) (PMMA) were purchased from Aldrich (Milwaukee, Wis., USA) and used without further purification. Dialysis tubing was commercially obtained from Spectrum.

To prepare NIPAAm-co-AA particles, a procedure similar to that described by Kratz, et al. and Pelton (R. Pelton, Adv. Colloid Interf. Sci., 85, 1 (2000).) was used. 6.80 g of NIPAAm (60 mmol), 0.5 g of SDS (1.7 mmol) and 0.14 g of MBA (0.91 mmol) were dissolved in 470 g of double distilled water, degassed with argon. The synthesis was carried out under argon atmosphere to exclude oxygen. After heating the solution to 75° C., 0.5 g of KPS (1.8 mmol) and 0.3 g of AA (4.2 mmol) in 30 g of water were added under gentle stirring. The reaction proceeded for 1 hour at constant temperature. The obtained NIPAAm-co-AA nanoparticles in aqueous solution were dialyzed with distilled water by using a dialysis membrane (celluSep®, molecular weight cut-off=5,000) for 24 hours in order to purify the product. This process results in NIPAAm-co-AA particles having a size of about 300 nm to about 1 μm, measured by the dynamic light scattering at room temperature.

Hardening of NIPAAm-co-AA particle was carried out by UV radiation. Briefly, 10 mL of NIPAAm-co-AA solution (10 wt %) was uniformly dispersed in a container to form a 1 mm layer. A UV source having a wavelength of about 365 nm was applied to the layer for 20 seconds at an intensity of about 120 W to harden the particles. Other embodiments can use irradiation of the UV source for shorter or longer periods of time, with the intensity of the light increasing or decreasing depending on the amount of time.

Hardened NIPAAm-co-AA particles were isolated and placed on a clean framed glass plate in a single layer having a close-packed lattice arrangement. Then, a tetrahydrofuran (THF) solution of poly(methyl methacrylate) (MW=~350, 000) was slowly added single layer and held by the framed glass plate until the single layer of particles was covered by the THF solution. The particles and solution were dried at room temperature for more than 24 hours and successively vacuum dried for more than 24 hours at the same temperature to form a body of joined particles.

To cut the top of the particles, the body of particles was cooled with liquid $N_2$. After cooling, a top surface of the particles was cut off by using a horizontally incident computer controlled laser cutter to remove about 50 μm to about 100 μm thickness of shell from the top to newly expose the expandable core.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

Figure 5:
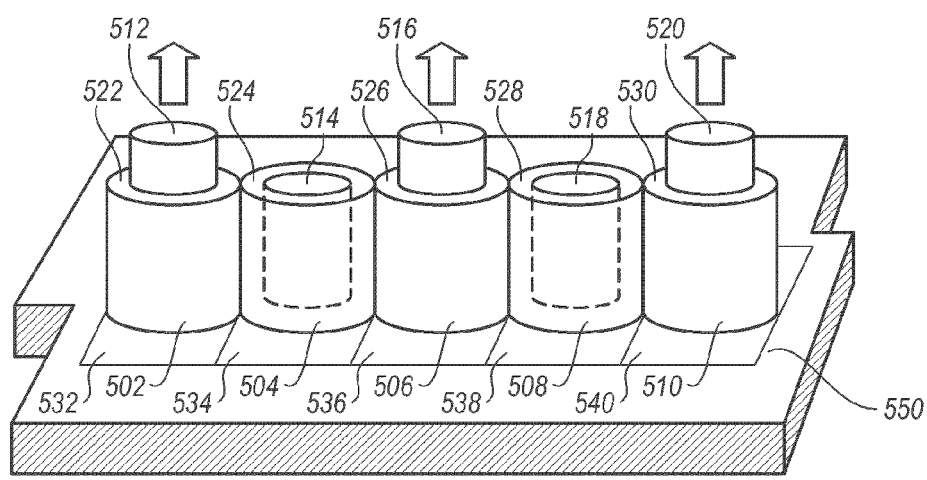
FIG. 5 is a perspective schematic view of an illustrative embodiment of arranging actuators on a surface.

FIG. 5 is a perspective schematic view of an illustrative embodiment for arranging multiple actuator units 502, 504, 506, 508, 510 together. Using actuator unit 502 as an example, actuator unit 502 has a shell 512 and a core 522. Similarly, actuator units 504, 506, 508 and 510 have cores 514, 516, 518 and 520, respectively, and shells 524, 526, 528 and 530, respectively. Each actuator 502, 504, 506, 508, 510 rests on a surface 550. In one embodiment, the actuators 502, 504, 506, 508, 510 are densely arranged so that the actuators do not have to be bonded to the surface 550. However, in another embodiment, the shells 522, 524, 526, 528, 530 of each actuator unit 502, 504, 506, 508, 510 can be affixed to the surface 550 before or after the opening is formed in the shell. In still another embodiment, where the shells 522, 524, 526, 528, 530 include an opening on the bottom of the actuator, the bottom of the cores 512, 514, 516, 518, 520 can be affixed to the surface 550. In one embodiment, a NIPAAm shell and/or core can be grafted onto surface 550 by treating the surface 550 with a silane coupling agent with a dithiocarbamate group. The NIPAAm is then photopolymerized in the presence of a crosslinking agent, BisAAm to generate a crosslinked PNIPAAm layer on the surface 550.

FIG. 5 also illustrates that actuator units 502, 504, 506, 508, 510 can be attached together. Thus, in one embodiment, methods for forming actuators can include attaching a shell (e.g., 522) of a first actuator (e.g., 502) to the shell (e.g., 524) of a second actuator (e.g., 504). In one embodiment, the actuators 502, 504, 506, 508, 510 are affixed to a surface 550 and then impregnated with a joining polymer solution (not shown). The joining polymer for joining actuator units together include, but are not limited to, polystyrene (PS), poly(methyl methacrylate) (PMMA), poly(ethyl methacrylate) (PEMA), poly(methyl acrylate) (PMA), polycarbonate (PC), or a combination thereof. These amorphous polymers generally have properties of cohesiveness and dimensional stability under a wide range of temperature. The latter characteristic is useful when at least a portion of each shell 522, 524, 526, 528, 530 is removed to form the opening. In one embodiment, the actuators 502, 504, 506, 508, 510 are affixed to a surface 550 and the shells 522, 524, 526, 528, 530 of the actuators 502, 504, 506, 508, 510 are attached to each other and then any of the methods described above applied to remove the portion of the shells 522, 524, 526, 528, 530 together as a group to form openings to expose the cores 512, 514, 516, 518, 520 in the shells.

FIG. 5 further illustrates that actuator units 502, 504, 506, 508, 510 can be arranged in a row, such that individual actuators units 502, 504, 506, 508, 510 are joined to each other in the pre-determined manner. Below each actuator unit 502, 504, 506, 508, 510 is shown a stimuli area 532, 534, 536, 538, 540, respectively. Stimuli areas 532, 534, 536, 538, 540 are illustrative of any type of stimuli that can be applied to the actuators 502, 504, 506, 508, 510 and can be any of the types of stimuli discussed herein (such as heat or light). Stimuli areas 532, 534, 536, 538, 540 are used to illustrate that a stimulus can be independently applied to each individual actuator unit 502, 504, 506, 508, 510 to activate or deactivate individual cores 512, 514, 516, 518, 520. In the example of FIG. 5, cores for actuators 502, 506, and 510 are activated while cores for actuators 504 and 508 are deactivated or resting. Thus, actuators 502, 504, 506, 508, 510 can be operated independently of each other.

Figure 6A:
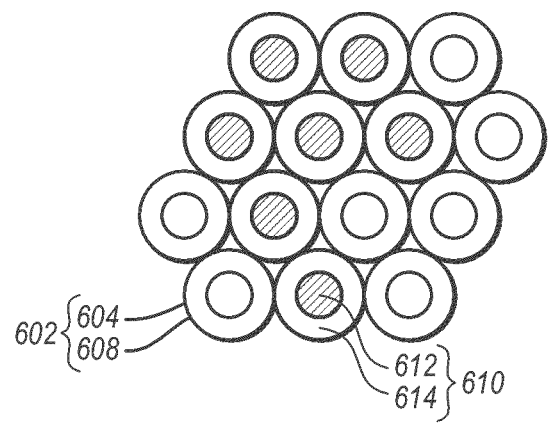
FIG. 6A is a top schematic view of an illustrative embodiment of arranging actuators on a surface.

FIG. 6A is a top schematic view of another illustrative embodiment for arranging actuators on a surface. FIG. 6A illustrates a plurality of actuator units e.g., 602 and 610 arranged in a closely packed lattice arrangement or array similar to a single layer face center cubic crystal structure. For ease of viewing, only some actuator units have reference numerals since in this embodiment, all of the actuators have the same construction. In this embodiment, each actuator unit 602, 610 has a shell 608, 614 with an exposed core 604, 612, respectively. This embodiment shows that some actuators 602 can be in the deactivated state while some actuators 610 can be in the activated stated and can be operated independently of each other. The activated state is illustrated having the core 612 shown having a hatched pattern.

Figure 6B:
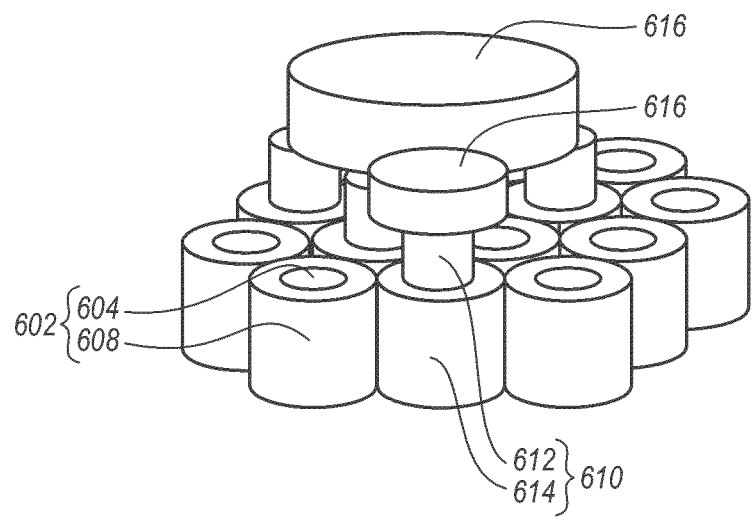
FIG. 6B is a perspective schematic view of the illustrative embodiment of arranging actuators of FIG. 6A.

FIG. 6B is a perspective schematic view of the illustrative embodiment for arranging actuators on a surface of FIG. 6A. FIG. 6B shows the independent activation/deactivation of the actuator units in further detail. For those actuators that are active, at least a portion of the core 612 is raised above the shell 614. For those actuators that are deactivated, the core 604 is substantially contained within a perimeter of the shell 608. This allows some or all of the actuators to be activated depending on whether the actuator is carrying a target cell that is ready to be harvested. In one embodiment, when only some part of the target cells are growing well and mature enough to be harvested, only the actuators that are under the mature target cells 616 can be independently activated to harvest the mature target cells, leaving unmatured target cells on deactivated actuators to continue to grow.

Figure 7:
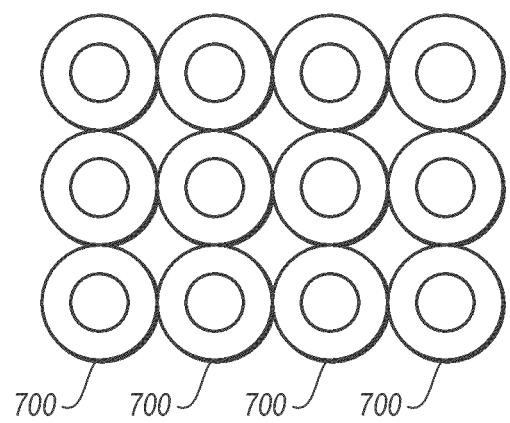
FIG. 7 is a top schematic view of an illustrative embodiment of arranging actuators.

FIG. 7 is a top schematic view of another illustrative embodiment for arranging actuators on a surface. FIG. 7 illustrates a plurality of actuator units 700 arranged in a closely packed lattice arrangement similar to a single layer simple cubic crystal structure. As with other arrangement described herein, the actuator units 700 can be independently activated/deactivated as desired. The surface upon which the actuators are affixed can be part of a container used to hold the target cells. The container can be, but is not limited to, a culture dish, a flask, or any kind of container usable for cell culture.

Turning back to FIG. 5, stimuli areas 532, 534, 536, 538, 540 are representative of one or more activating devices applying stimuli to an actuator 502, 504, 506, 508, 510. An activating device generates the one or more stimuli to place the core in the deactivated and/or activated state. Even though the stimuli areas 532, 534, 356, 538, 540 are shown under the actuators 502, 504, 506, 508, 510, this is only representative of the application of stimuli and does not reflect the exact location of an activating device that produces the stimuli. In one embodiment, the activating device is able to generate the one or more stimuli substantially near the actuator. Suitable activating devices depend on the type of stimuli-responsive polymer being used for the core and/or shell. The stimuli can be transmitted from above, to the side, and/or under the actuators. The activating device and the surface holding the actuators may be located near each other so that the stimuli can reach the actuators quickly. For example, if the stimulus is heat or light, the activating device can include heating or lighting elements located substantially near each actuator. Where the phase change of the stimuli-responsive polymer of the core reacts with only a slight change of a temperature or light, the activating device can operate for only a short amount of time, reducing or minimizing damage to target cells. In one illustrative embodiment, the activating device may be operated for about 1 second to about 30 seconds to activate one or more actuators.

In embodiments where the activating device is a heating/cooling device, various heating/cooling devices may be used including, but not limited to, PLC (planar lightwave circuit), a ceramic heater, a micro cooling/heating device, peltier elements, or a combination thereof. In various embodiments, a lattice-shaped micro matrix is used to install cooling/heating elements in a grid formation. The micro matrix can correspond to a lattice-shaped arrangement of actuator units so that a cooling/heating element can be located under or over each actuator unit. Since each cooling/heating element on the matrix controls temperature accurately, each actuator can be activated/deactivated as desired. In one embodiment, when only some part of the target cells are mature and ready to be harvested, the actuators underneath the mature target cells can be activated to allow the mature target cells to be harvested efficiently. FIGS. 6A and 6B illustrate this concept. Of course, when the cell culture goes well and all target cells are mature, all of the target cells can be harvested at the same time.

In embodiments where the activating device is a photo-generating device, a NIR irradiator can be applied. Illustratively, near infrared (NIR) radiation can be applied having a wavelength of, for example, about 700 nm to about 1,400 nm, or about 725 nm to about 1,000 nm, or about 750 nm to about 800 nm, as illustrative examples.

As mentioned before, the activating device provides the required stimulus to the actuators quickly, so that the stimulus does not damage the target cells. The activating device can be operated to activate none, all or only a portion of the actuators located on a surface. In various embodiments, the actuators can be operated to act independently of each other. When the actuators are activated, the cores are able to move in and out of the at least one opening of the shell similar to a piston motion so that the actuators push the target cells upward. The mechanical movement breaks adhesiveness that may have formed between target cells and cells adjacent to the target cells. In some embodiments, the lifting action breaks physical bonds existing between adjacent target cells, or at least loosens the bonds existing therebetween. In some embodiments, repeated actuation of the actuators may be necessary so that the core goes through multiple cycles of activation/deactivation (much like a piston action). In one embodiment, the number of cycles to loosen the bonds between target cells and adjacent target cells is about 1 cycle to about 10 cycles over a period of about 30 seconds. The number of cycles may depend on a number of factors such as the size of the actuator, the type of target cell that is located on the actuator, and the density of the actuators. For example, larger actuators may provide more lift force so that fewer cycles are required versus smaller actuators that may provide less lift force. In another example, certain types of target cells may experience greater adhesion with the actuator than other types of target cells due to difference in extracellular matrix, functional groups, proteins or other binding sites that may exist on the wall of the target cell. In yet another example, target cells that are closer together may require more lifting cycles to loosen the bonds between them versus target cells that are further apart and may not experience as great of bonding forces therebetween. Despite the repeated movement of the core, the actuators are able to keep the target cells from becoming damaged.

In one embodiment, the lifting action of the actuators serves to loosen target cells that are ready for harvest. After the target cells are loosened from adjacent cells, the loosened target cells can be collected by a known technique, such as scraping, tweezers, filtering, and the like. As discussed above, the target cells may be mature cultured cells, undesirable cells, or any cell that is desired to be harvested. Generally, a cell that has been loosened by an actuator is referred to as a "target cell." The lifting action of the actuators assists harvesting of target cells by loosening bonds and, in some case, raising target cells higher than other cells for ease in grasping with an instrument, such as tweezers.

In another embodiment, some of the actuators may have feeder cells located thereon while other actuators have adhesive cells (i.e., target cells) that culture while adhering to the feeder cells. When the adhesive cells (i.e., target cells) are mature, the actuators on which the adhesive cells (i.e., target cells) are located can be activated to loosen the adhesive cells for culture. A suspension fluid can be poured into culture container to suspend the loosened adhesive cells (i.e., target cells). The suspension fluid can be a culture medium such as, but not limited to saline, bovine serum, nutrients, and the like. The suspension fluid raises the loosened adhesive cells (i.e., target cells) into suspension above the other cells in the culture. In one embodiment, raising the loosened adhesive cells (i.e., target cells) above the other cells allows for the loosened target cells to be more easily grasped by tweezers, filtered by a nylon mesh filter (e.g., manufactured by Miltenyi biotech), and the like, for harvesting.

Various types of cells can be cultured with actuator systems disclosed herein. Illustrative types of cells that can be cultured and isolated include adhesive cells such as, but not limited to, stem cells, follicle cells, epidermal cells, osteoblasts, and the like. Conventional cell culture mediums can also be used since the actuators are stable in most mediums.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly of the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

The invention claimed is:

1. A system for harvesting target cells, the system comprising:
 a cell culture dish that includes one or more actuators, each actuator having a core and a shell at least partially surrounding the core that defines a longitudinal axis, the shell defining a top surface and having at least one opening,
 in a first condition, the core being positioned and dimensioned in the shell such that the top surface of the shell and the core are configured to associate with one or more target cells in culture, and in a second condition, the core being positioned and dimensioned in the shell such that the core is configured to expand and displace out of the shell in a direction along the longitudinal axis through the at least one opening to lift up one or more target cells in culture positioned over the core and to break an adhesion between the one or more target cells and the top surface of the shell, wherein at least the core comprises a stimuli-responsive polymer configured to expand or contract in response to one or more stimuli and having a first portion configured to associate with the one or more target cells in culture, wherein in response to a first stimulus to place the core in the first condition, the stimuli-responsive polymer is configured to contract such that the first portion of the core is substantially contained within a perimeter of the shell, and wherein in response to a second stimulus to place the core in the second condition, the stimuli-responsive polymer is configured to expand such that the first portion of the core expands through the at least one opening of the shell and is located outside the perimeter of the shell.

2. The system as recited in claim 1, wherein the stimuli-responsive polymer of the core is at least one of:
a thermo-responsive polymer, or
a photo-responsive polymer.

3. The system as recited in claim 2, wherein the thermo-responsive polymer of the core is a polymer selected from the group of poly-N-isopropylacrylamide, poly-vinylmethyl-ether, poly-dimethyl acrylamide, poly-methacrylate, poly-acrylic acid, or a combination thereof.

4. The system as recited in claim 2, wherein the photo-responsive polymer of the core is a co-polymer formed from N-isopropylacrylamide and acrylic acid, or a hydrogel that contains gold or iron nanoparticles.

5. The system as recited in claim 1, wherein in response to a second stimulus, the shell does not change shape as the core expands through the at least one opening of the shell.

6. The system as recited in claim 1, wherein the shell comprises a stimuli-responsive polymer, wherein the stimuli-responsive polymer of the shell and the stimuli-responsive polymer of the core are made from a same co-polymer that is responsive to one or more stimuli.

7. The system as recited in claim 1, wherein shells of two or more actuators are attached by a joining polymer.

8. The system as recited in claim 7, wherein the joining polymer comprises one or more of polystyrene, poly(methyl)methacrylate, poly(ethyl)methacrylate, poly(methyl)acrylate, polycarbonate, or a combination thereof.

9. The system as recited in claim 1, wherein a diameter of the shell is from about 500 nm to about 5 mm.

10. The system as recited in claim 1, wherein a diameter of the core is from about 300 nm to about 4.5 mm.

11. The system as recited in claim 1, wherein the one or more actuators are arranged on a surface in at least one of:
a row;
an array; or
a lattice.

12. The system as recited in claim 1, further comprising an activating device to generate the one or more stimuli, the activating device being able to generate the one or more stimuli substantially near the one or more actuators.

13. The system as recited in claim 1, wherein the one or more stimuli can be applied independently to different actuators.

* * * * *

UNITED STATES PATENT AND TRADEMARK OFFICE
CERTIFICATE OF CORRECTION

PATENT NO. : 8,569,048 B2
APPLICATION NO. : 12/631623
DATED : October 29, 2013
INVENTOR(S) : Fujimoto It is certified that error appears in the above-identified patent and that said Letters Patent is hereby corrected as shown below:

On the Title Page, in Item (56), under "OTHER PUBLICATIONS", in Column 2, Line 4, delete "et al" and insert -- et al., --, therefor.

On the Title Page, in Item (56), under "OTHER PUBLICATIONS", in Column 2, Line 7, delete "et al" and insert -- et al., --, therefor.

On the Title Page, in Item (56), under "OTHER PUBLICATIONS", in Column 2, Line 10, delete "et al" and insert -- et al., --, therefor.

On the Title Page, in Item (56), under "OTHER PUBLICATIONS", in Column 2, Line 13, delete "et al" and insert -- et al., --, therefor.

On the Title Page, in Item (56), under "OTHER PUBLICATIONS", in Column 2, Line 16, delete "et al" and insert -- et al., --, therefor.

On the Title Page, in Item (56), under "OTHER PUBLICATIONS", in Column 2, Line 19, delete "et al" and insert -- et al., --, therefor.

On Title Page 2, in Item (56), under "OTHER PUBLICATIONS", in Column 1, Line 1, delete "et al" and insert -- et al., --, therefor.

On Title Page 2, in Item (56), under "OTHER PUBLICATIONS", in Column 1, Lines 2-3, delete "Poly(N-isopropylarcrylamide)" and insert -- Poly(N-isopropylacrylamide) --, therefor.

On Title Page 2, in Item (56), under "OTHER PUBLICATIONS", in Column 1, Line 5, delete "et al" and insert -- et al., --, therefor.

On Title Page 2, in Item (56), under "OTHER PUBLICATIONS", in Column 1, Line 6, delete "et al" and insert -- et al., --, therefor.

Signed and Sealed this
First Day of April, 2014

Michelle K. Lee
*Deputy Director of the United States Patent and Trademark Office*

CERTIFICATE OF CORRECTION (continued)
U.S. Pat. No. 8,569,048 B2

On Title Page 2, in Item (56), under "OTHER PUBLICATIONS", in Column 1, Line 9, delete "et al" and insert -- et al., -- therefor.

On Title Page 2, in Item (56), under "OTHER PUBLICATIONS", in Column 1, Line 13, delete "et al" and insert -- et al., --, therefor.

On Title Page 2, in Item (56), under "OTHER PUBLICATIONS", in Column 1, Line 19, delete "et al" and insert -- et al., --, therefor.

On Title Page 2, in Item (56), under "OTHER PUBLICATIONS", in Column 1, Line 22, delete "et al" and insert -- et al., --, therefor.

On Title Page 2, in Item (56), under "OTHER PUBLICATIONS", in Column 2, Line 4, delete "et al" and insert -- et al., --, therefor.

On Title Page 2, in Item (56), under "OTHER PUBLICATIONS", in Column 2, Line 8, delete "et al" and insert -- et al., --, therefor.

On Title Page 2, in Item (56), under "OTHER PUBLICATIONS", in Column 2, Line 25, delete "Aug. 21," and insert -- Aug. 28, --, therefor.

In the Specification

In Column 9, Line 63, delete "shell 512 and a core 522." and insert -- shell 522 and a core 512. --, therefor.

In Column 13, Line 9, delete "biotech)," and insert -- biotec), --, therefor.